United States Patent
Shukla et al.

(10) Patent No.: US 8,019,042 B2
(45) Date of Patent: Sep. 13, 2011

(54) MEDICAL IMAGING PROCESSING AND CARE PLANNING SYSTEM

(75) Inventors: Himanshu P. Shukla, Lafayette, CA (US); John R. Zaleski, Elkton, MD (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 712 days.

(21) Appl. No.: 12/180,736

(22) Filed: Jul. 28, 2008

(65) Prior Publication Data

US 2009/0262894 A1 Oct. 22, 2009

Related U.S. Application Data

(60) Provisional application No. 61/046,918, filed on Apr. 22, 2008.

(51) Int. Cl.
*A61N 5/10* (2006.01)
*G06K 9/00* (2006.01)

(52) U.S. Cl. .......................... 378/65; 382/130

(58) Field of Classification Search ................ 378/4, 65, 378/64, 95, 108, 112, 97, 207; 382/128, 382/130, 131, 132
See application file for complete search history.

(56) References Cited

U.S. PATENT DOCUMENTS

| | | | |
|---|---|---|---|
| 5,926,568 A | 7/1999 | Chaney et al. | |
| 7,873,403 B2 * | 1/2011 | Lachner et al. | 600/425 |
| 7,893,938 B2 * | 2/2011 | Aharon | 345/422 |
| 7,920,152 B2 * | 4/2011 | Fram et al. | 345/661 |
| 2007/0165779 A1 * | 7/2007 | Chen et al. | 378/65 |
| 2007/0189455 A1 | 8/2007 | Allison | |
| 2008/0002811 A1 | 1/2008 | Allison | |
| 2008/0031406 A1 | 2/2008 | Yan et al. | |
| 2009/0028403 A1 * | 1/2009 | Bar-Aviv et al. | 382/128 |

* cited by examiner

*Primary Examiner* — Irakli Kiknadze
(74) *Attorney, Agent, or Firm* — Alexander J Burke

(57) ABSTRACT

A system automatically compares radiotherapy 3D X-Ray images and subsequent images for update and re-planning of treatment and for verification of correct patient and image association. A medical radiation therapy system and workflow includes a task processor for providing task management data for initiating image comparison tasks prior to performing a session of radiotherapy. An image comparator, coupled to the task processor, in response to the task management data, compares a first image of an anatomical portion of a particular patient used for planning radiotherapy for the particular patient, with a second image of the anatomical portion of the particular patient obtained on a subsequent date, by image alignment and comparison of image element representative data of aligned first and second images to determine an image difference representative remainder value and determines whether the image difference representative remainder value exceeds a first predetermined threshold. An output processor, coupled to the image comparator, initiates generation of an alert message indicating a need to review planned radiotherapy treatment for communication to a user in response to a determination the image difference representative remainder value exceeds a predetermined threshold.

17 Claims, 8 Drawing Sheets

| CTP | Pixel Element | CTm | Difference 2-1 | RSS |
|---|---|---|---|---|
| -1.7E+07 | 9315 | -1.7E+07 | 0 | 0.005119638 |
| -1.6E+07 | 9316 | -1.6E+07 | -197379 | |
| -1.6E+07 | 9317 | -1.6E+07 | -197379 | |
| -1.6E+07 | 9318 | -1.6E+07 | -197379 | |
| -1.6E+07 | 9319 | -1.6E+07 | -197379 | |
| -1.7E+07 | 9320 | -1.6E+07 | -263172 | |
| -1.7E+07 | 9321 | -1.6E+07 | -263172 | |
| -1.7E+07 | 9322 | -1.6E+07 | -263172 | |
| -1.7E+07 | 9323 | -1.6E+07 | -263172 | |
| -1.6E+07 | 9324 | -1.6E+07 | -65793 | |
| -1.6E+07 | 9325 | -1.6E+07 | -197379 | |
| -1.6E+07 | 9326 | -1.6E+07 | -197379 | |
| -1.6E+07 | 9327 | -1.6E+07 | -65793 | |
| -1.6E+07 | 9328 | -1.6E+07 | 65793 | |
| -1.6E+07 | 9329 | -1.6E+07 | 65793 | |
| -1.6E+07 | 9330 | -1.6E+07 | 65793 | |
| -1.6E+07 | 9331 | -1.6E+07 | 65793 | |
| -1.6E+07 | 9332 | -1.6E+07 | 0 | |
| -1.6E+07 | 9333 | -1.6E+07 | 0 | |
| -1.6E+07 | 9334 | -1.6E+07 | 0 | |
| -1.6E+07 | 9335 | -1.6E+07 | 0 | |
| -1.6E+07 | 9336 | -1.6E+07 | 131586 | |
| -1.6E+07 | 9337 | -1.6E+07 | 131586 | |
| -1.6E+07 | 9338 | -1.6E+07 | -131586 | |
| -1.6E+07 | 9339 | -1.6E+07 | -131586 | |
| -1.6E+07 | 9340 | -1.6E+07 | -131586 | |
| -1.6E+07 | 9341 | -1.6E+07 | 0 | |
| -1.6E+07 | 9342 | -1.6E+07 | 0 | |

MEDICAL IMAGING PROCESSING AND CARE PLANNING SYSTEM

This is a non-provisional application of provisional application Ser. No. 61/046,918 filed Apr. 22, 2008, by H. P. Shukla et al.

FIELD OF THE INVENTION

This invention concerns a medical radiation therapy system and workflow involving comparing images of patient anatomy used for planning radiotherapy to trigger review of planned radiotherapy treatment, patient identity verification and associated alert message generation.

BACKGROUND OF THE INVENTION

In known systems for patient radiotherapy treatment, 3D X-Ray images are taken to plan a treatment process. Subsequent images (of which many dozens may be taken) may be used to position the patient, but are typically not used to re-plan and refine the treatment process, nor are subsequent images used to incrementally or in ensemble, determine anatomical changes (substantive or otherwise) with respect to an initial planning image. Known systems for patient radiotherapy treatment are also vulnerable to mis-identifying images or a patient associated with an image. This results in potentially ineffective or impaired radiotherapy treatment. A system according to invention principles addresses these deficiencies and related problems.

SUMMARY OF THE INVENTION

A system enables detection and more accurate treatment of secondary occurrences of cancerous lesions in radiotherapy patients, for example, by automatic comparison of radiotherapy 3D X-Ray images taken on different treatment occasions and stages for update and re-planning of treatment and for verification of correct patient and image association. A medical radiation therapy system and workflow includes a task processor for providing task management data for initiating image comparison tasks prior to performing a session of radiotherapy. An image comparator, coupled to the task processor, in response to the task management data, compares a first image of an anatomical portion of a particular patient used for planning radiotherapy for the particular patient, with a second image of the anatomical portion of the particular patient obtained on a subsequent date, by image alignment and comparison of image element representative data of aligned first and second images to determine an image difference representative value and determines whether the image difference representative value exceeds a first predetermined threshold. An output processor, coupled to the image comparator, initiates generation of an alert message indicating a need to review planned radiotherapy treatment for communication to a user in response to a determination that the image difference representative value exceeds a predetermined threshold.

BRIEF DESCRIPTION OF THE DRAWINGS

FIG. 6 illustrates a brief comparison between pixel data, according to invention principles.

DETAILED DESCRIPTION OF THE INVENTION

Figure 1:
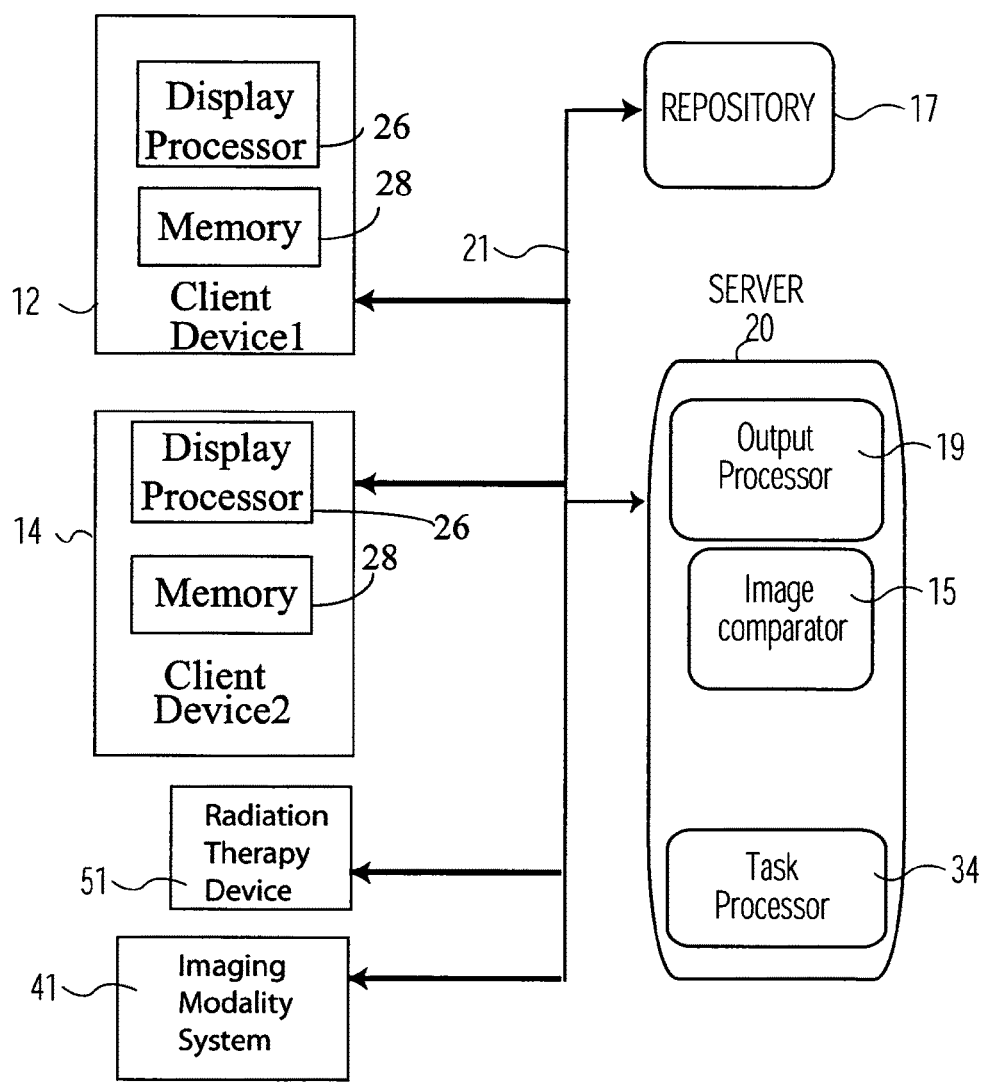
FIG. 1 shows a medical radiation therapy and workflow system supporting review and update of radiotherapy treatment, according to invention principles.

A system enables detection and more accurate treatment of secondary occurrences of cancerous lesions in radiotherapy patients, for example. In radiotherapy, 3D X-Ray initial images are acquired to plan a treatment process. Subsequent images (of which many dozen may be taken) may be used to position a patient, but are typically not used to re-plan and refine the treatment process, nor are subsequent images used to incrementally or in ensemble, determine anatomical changes (substantive or otherwise) with respect to an initial planning image. The system provides updated and re-planned treatment based on a more accurate assessment of patient condition and targeting of affected cancerous regions. Furthermore, the system provides an indication of incorrect patient selection based on a probability measure indicating a likelihood of correct image-to-patient association derived from a measure of a degree of similarity of images. The system advantageously mutually compares subsequent patient medical images to verify patient identity and associate and correlate peculiarities within patient image content to distinguish different patients and identify a patient.

A processor as used herein is a device and/or set of machine-readable instructions for performing tasks. A processor comprises any one or combination of, hardware, firmware, and/or software. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be coupled (electrically and/or as comprising executable components) with any other processor enabling interaction and/or communication there-between. A display processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps (e.g., of FIG. 8) herein may be performed automatically or wholly or partially in response to user command. An activity (including a step) performed automatically is performed in response to executable instruction or device operation without user direct initiation of the activity. Workflow comprises a sequence of tasks performed by a device or worker or both. An object or data object comprises a grouping of data, executable instructions or a combination of both or an executable procedure.

A workflow processor, as used herein, processes data to determine tasks to add to, or remove from, a task list or modifies tasks incorporated on, or for incorporation on, a task list. A task list is a list of tasks for performance by a worker or device or a combination of both. A workflow processor may or may not employ a workflow engine. A workflow engine, as used herein, is a processor executing in response to predetermined process definitions that implement processes responsive to events and event associated data. The workflow engine implements processes in sequence and/or concurrently, responsive to event associated data to determine tasks for performance by a device and or worker and for updating task lists of a device and a worker to include determined tasks. A process definition is definable by a user and comprises a sequence of process steps including one or more, of start, wait, decision and task allocation steps for performance by a device and or worker, for example. An event is an occurrence affecting operation of a process implemented using a process definition. The workflow engine includes a process definition function that allows users to define a process that is to be followed and includes an Event Monitor, which captures events occurring in a Healthcare Information System. A processor in the workflow engine tracks which processes are running, for which patients, and what step needs to be executed next, according to a process definition and includes a procedure for notifying clinicians of a task to be performed, through their worklists (task lists) and a procedure for allocating and assigning tasks to specific users or specific teams.

FIG. 1 shows medical radiation therapy and workflow system 10 supporting review and update of radiotherapy treatment. System 10 includes processing devices (e.g., workstations or portable devices such as notebooks, Personal Digital Assistants, phones) 12 and 14 that individually include a display processor 26 and memory 28. System 10 also includes at least one repository 17, radiation therapy device 51, imaging modality device (such as an MR (magnetic resonance), CT scan, X-ray or Ultra-sound device) 41 and server 20 intercommunicating via network 21. Display processor 26 provides data representing display images comprising a Graphical User Interface (GUI) for presentation on processing devices 12 and 14. At least one repository 17 stores medical image studies for multiple patients. A medical image study individually includes multiple image series of a patient anatomical portion which in turn individually include multiple images. Server 20 includes task processor 34, image comparator 15 and output processor 19.

Task processor 34 provides task management data for initiating image comparison tasks prior to performing a session of radiotherapy using radiotherapy device 51. Image comparator 15, coupled to task processor 34, in response to the task management data, compares a first image of an anatomical portion of a particular patient used for planning radiotherapy for the particular patient, with a second image of the anatomical portion of the particular patient obtained on a subsequent date. Image comparator 15 does this by image alignment and comparison of image element representative data of aligned first and second images to determine an image difference representative value and by determining whether the image difference representative value exceeds a first predetermined threshold. Output processor 19, coupled to image comparator 15, initiates generation of an alert message indicating a need to review planned radiotherapy treatment for communication to a user in response to a determination the image difference representative value exceeds a predetermined threshold.

Figure 2:
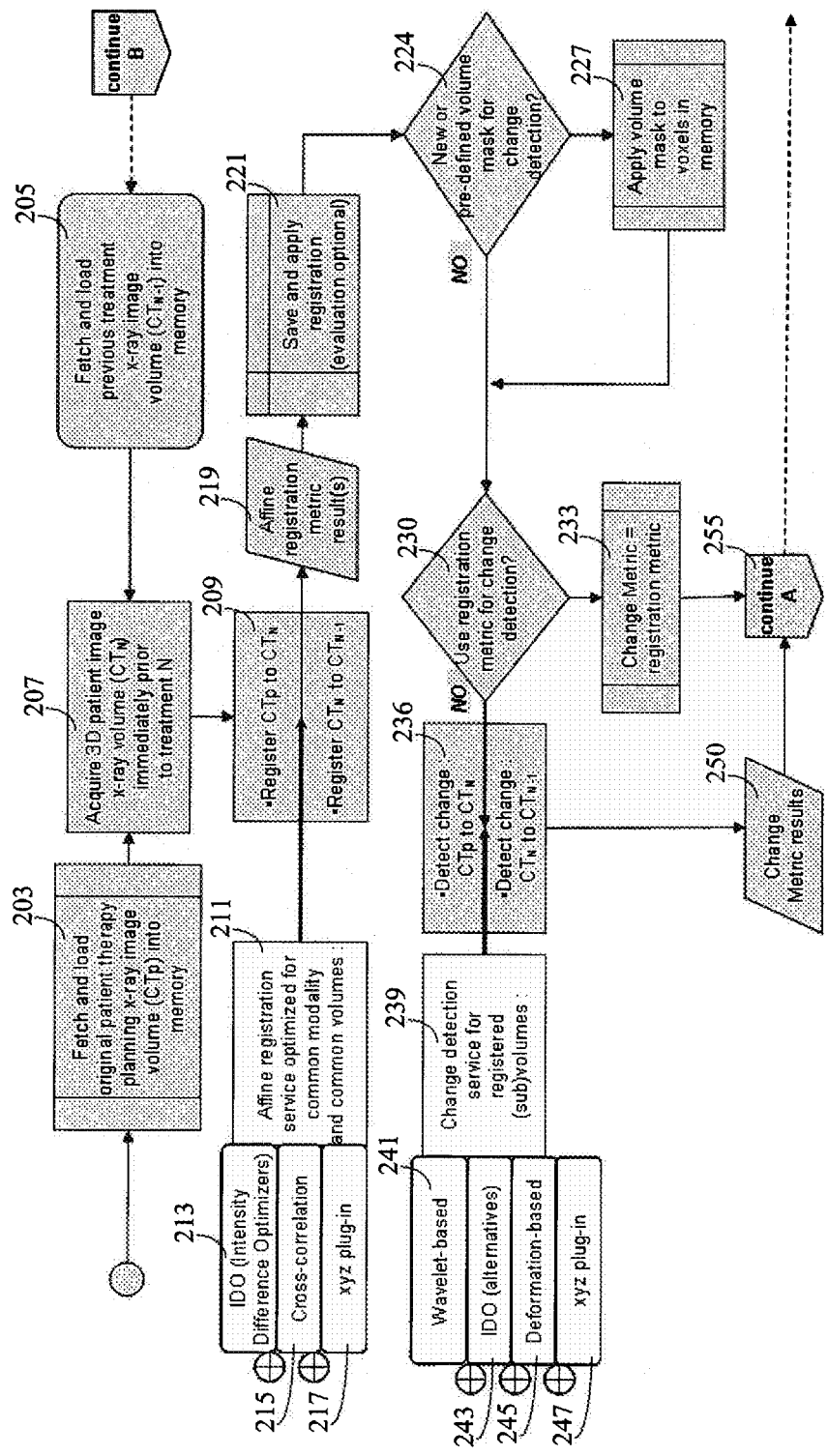
FIGS. 2 and 3 show a flowchart of a process performed by a medical radiation therapy and workflow system involving image comparison, according to invention principles.
Figure 3:
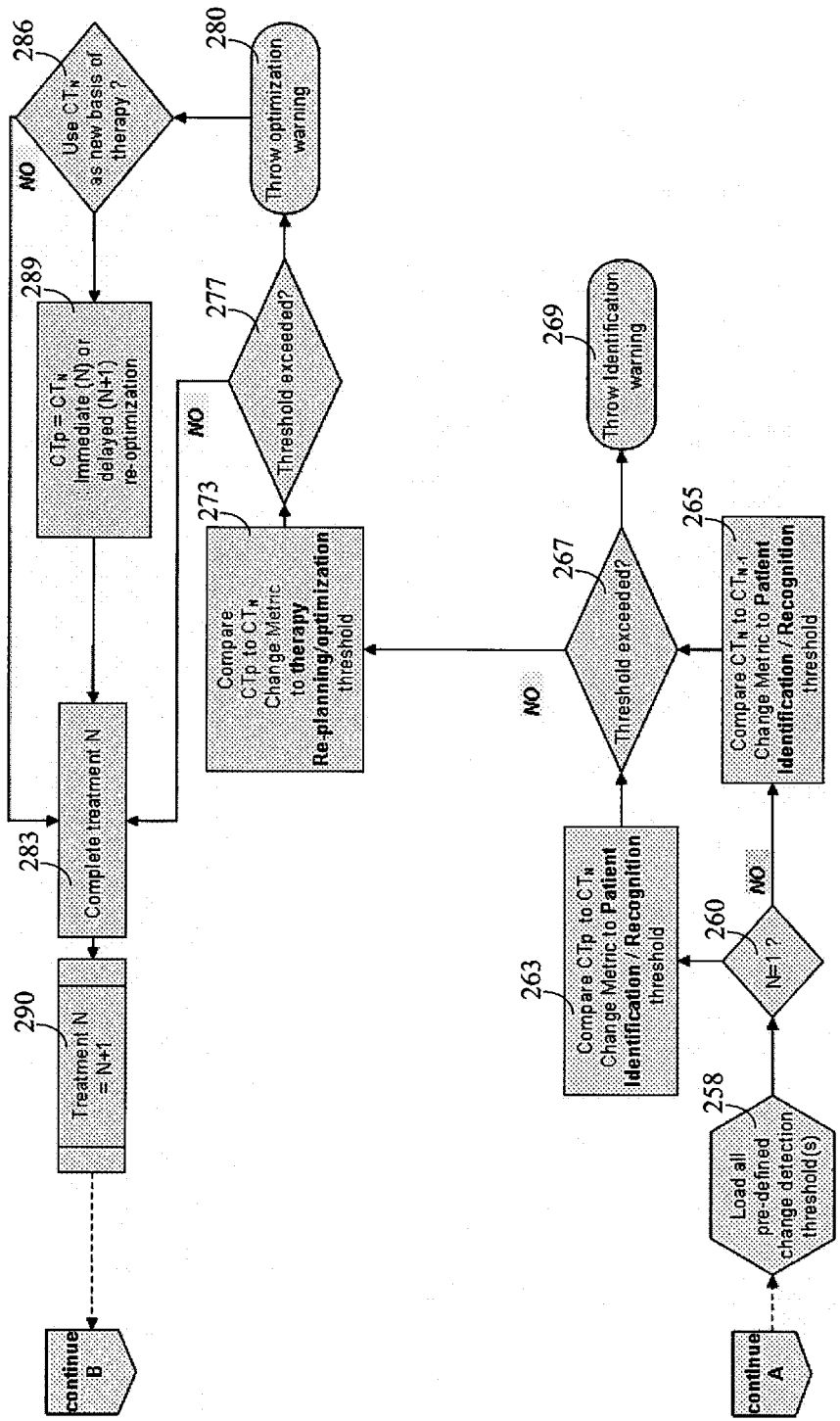

FIGS. 2 and 3 show a flowchart of a process performed by medical radiation therapy and workflow system 10 involving image comparison supporting review and update of planned radiotherapy treatment. In step 203 image comparator 15 (FIG. 1) acquires data representing X-Ray, CT scan or other images (CTp images) for planning patient radiotherapy treatment. The other images may comprise MR, or Ultrasound images, for example. The planning images represent 3D patient anatomical volumes and determine initial targeting of radiotherapy for cancer treatment. In step 207, image comparator 15, in response to initiation of radiotherapy treatment, acquires subsequent X-Ray images (CTn images, where n represents the number of the subsequent image) obtained by imaging device 41 most recently prior to treatment (treatment n of a series of treatments). The CTp planning images are registered (aligned) with the CTn subsequent images in step 209 by comparator 15 using one of multiple different known techniques, such as a wavelet-based transformation process involving transformation of raw images into low-pass and high-pass components for rapid association and comparison. An example of a wavelet-based transformation using the Haar basis functions to decompose an image into average and differential components is shown in FIG. 5.

Figure 5:
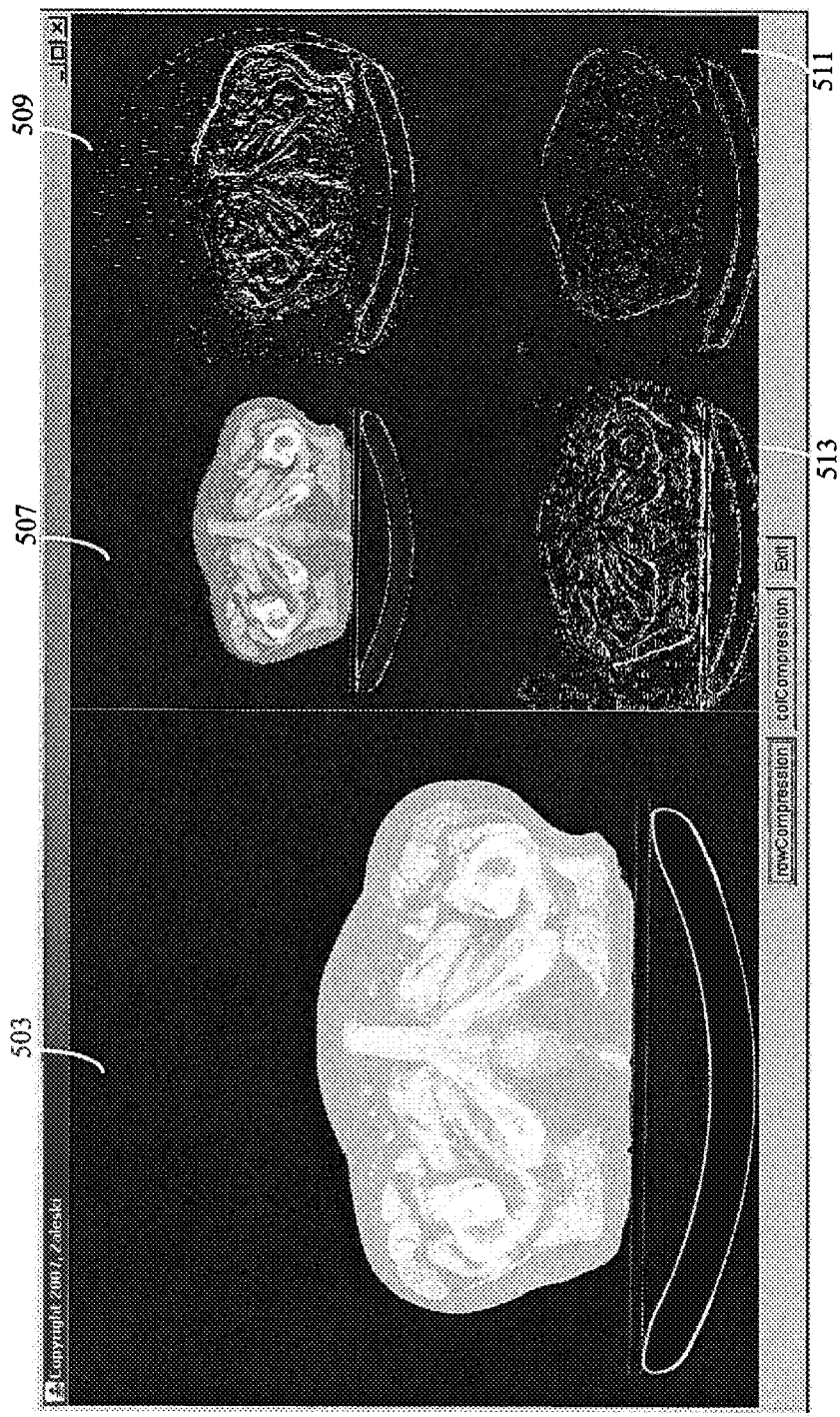
FIG. 5 illustrates anatomical image comparison, according to invention principles.

FIG. 5 illustrates anatomical image comparison and presents a planning image used to plan radiotherapy dosing and geometry of a patient. Image 503 represents original, raw pixel data from a patient X-Ray and represents a slice of a 3D planning CT. Images 507, 509, 511 and 513 represent, the average pixel values; the row-wise difference; the row-column differences; and the column-wise difference in pixel values, respectively. Comparison between these decomposed images with subsequent (CTn) images is performed by image comparator 15 to determine threshold differentials efficiently with relatively few data points in an initial comparison to determine whether a significant difference in any two images (CTp, CTn) exists requiring further analysis. Images 507, 509, 511 and 513 represent a first-order reduction using Haar wavelet transformation. Image 507 is an average image comprising a first order reduction showing the sum average of pixel components. Image 509 represents the difference of image column elements between two images. Image 513 represents the difference of image row elements between two images. Image 511 represents the difference of image row and column elements between two images. The Haar transformation is one reduction and registration process of multiple different processes that may be used for analyzing raw pixel data to provide a reduced information (smaller sample) data set requiring less processing power for analysis.

The registration processes of FIG. 2 that are usable also include intensity difference optimization 213, cross-correlation 215 and Cartesian coordinate transformation 217 to provide image Affine registration in step 211 (image transformation and sub-region alignment). In addition, in step 205 image comparator 15 registers subsequent images CTn−1 with respect to the CTn images (subsequent images CTn−1 are acquired after CTp images but prior to CTn images). Thereby, image comparator 15 in step 209 determines two registration metrics 219 that comprise a comparison or degree of correlation between two images to establish the degree of sameness (or, conversely, the degree of difference). The two registration metrics comprise a difference (or residual) between the transformed planning and subsequent images (CTp and CTn), and the subsequent incremental images (CTn and CTn−1), respectively. These differences, or residuals, are stored in step 221.

In step 224 it is determined if the predetermined 3D patient anatomical volume is new or has changed and if so applies a new or changed volume mask in step 227 or otherwise employs an original mask, for use in determining registered 3D image sub-volumes and comparing registration metrics with corresponding image change detection metrics of sub-volumes in step 230. Image comparator 15 in step 236 determines two image change detection metrics for comparison with corresponding image registration metrics. The two image change metrics represent detected change between registered sub volumes 239 of the transformed planning and subsequent images (CTp and CTn), and the subsequent incremental images (CTn and CTn−1), respectively. The image change detection metrics are determined using one of multiple different calculations including wavelet based 241, intensity difference optimization 243, deformation based 245 and Cartesian coordinate transformation 247 to more accurately determine changes in specific sub-regions of the acquired images.

In step 230 image comparator 15 compares the two registration metrics determined in step 209 with corresponding image change metrics determined in step 236 by one of multiple different measures to more accurately determine changes in specific sub-regions of the acquired images using a volume mask. If the registration metric and the change detection metric are determined to be equal in step 233, the registration metric for detected change is used in step 255, otherwise the change detection metric determined in step 236 is applied in step 250 and used in step 255 and in subsequent process steps. In step 258 (FIG. 3) image comparator 15 loads predetermined change detection thresholds from memory. The predetermined thresholds of acceptable levels of change detection, indicated as a type-I, type-II error threshold, are employed to determine the degree of acceptability of a measured change between a planning X-Ray image (CTp) and subsequent image (CTn). The first such subsequent image CTn is compared with the planning image CTp to determine the likelihood or similarity of the two images (thus, the case when n=1 (260)). This case is employed to verify the identity of the patient under treatment. A patient identification metric threshold quantifying the acceptable difference between the two images is established to define the likelihood of correct patient identity. For the case n=1 the detected difference between the CTp and CTn image derived in step 263 is compared with the patient identification threshold in step 267. An alert message is generated for communication to a user in step 269 if the threshold is exceeded.

Similarly, for other subsequent images that are taken (the case when n>1), an individual image is compared with subsequent image cases (i.e., CTn with CTn−1) in step 265 to derive a difference between the CTn and CTn−1 image which is compared with the similarity threshold establishing the likelihood of correct patient identity in step 267. If the image difference exceeds the similarity threshold, an alert message is generated for communication to a user in step 269 giving a notification to a physician (radiologist, oncologist) via a worklist (list of tasks) in a workflow managed system, for example. In one embodiment, a workflow warning is distributed through an automated workflow engine to a health information system (HIS).

In step 267, if it is determined the image difference does not exceed the similarity threshold, indicating subsequent image CTn, is substantially similar to other subsequent images CTn−1 and to the planning image CTp in terms of patient identification, a finer comparison is made in step 273 between the subsequent images and the planning image (i.e., the image used for planning radiotherapy treatment). In step 277 image comparator 15 compares the quantified image difference between the planning image CTp and the subsequent image CTn determined in step 273, with a clinically-specified re-planning and re-optimization threshold. If the threshold is not exceeded radiotherapy treatment sessions are continued as planned in treatments of step 283 (treatment n) and step 290 (treatment n+1) and associated treatment images are used in the FIG. 2 process step 205 as previously described. If it is determined in step 277 that the optimization threshold is exceeded, an optimization warning is generated for communication to a user in step 280 giving a notification to a physician (radiologist, oncologist) via a worklist in a workflow managed system, for example. In one embodiment, a workflow warning is distributed through an automated workflow engine to a health information system (HIS). In response to the similarity threshold being exceeded image comparator determines in step 286 whether the current planning image CTp is replaced with the current image CTn and used for updated radiotherapy planning. If it is determined to replace CTp with CTn in step 286, in step 289 the CTn image is replaced with a new image e.g., CTn+1 and the process continues with treatment as previously described in step 283. This process is repeated throughout treatment, and typically may involve the measurement of ~40 or more X-Ray images over the course of treatment, for example. If it is determined not to replace CTp with CTn in step 286, the process continues with treatment as previously described in step 283.

Figure 4:
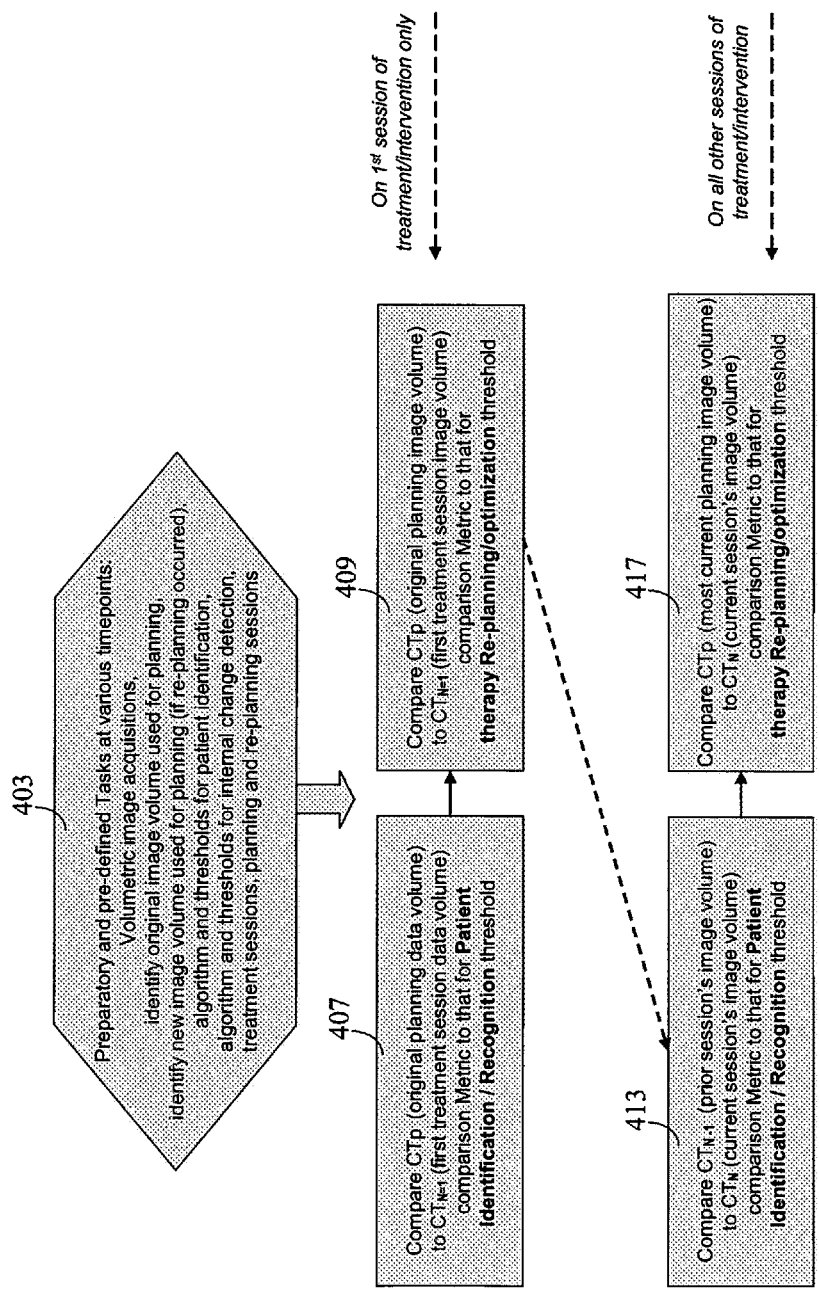
FIG. 4 shows a flowchart of an image comparison process performed by a medical radiation therapy and workflow system, according to invention principles.

FIG. 4 shows a flowchart of an image comparison process employed by medical radiation therapy and workflow system 10 and usable in the process of FIGS. 2 and 3. In step 403, image comparator 15 performs preparatory and predetermined tasks at various time points. These tasks include acquisition of Volumetric image data, identification of an original image volume used for planning and identification of a new image volume used for planning (if re-planning occurred). Image comparator 15, in response to predetermined configuration data, selects an algorithm and thresholds for use in patient identification, selects algorithm and thresholds for internal change detection and acquires treatment sessions, planning and re-planning session image data (e.g., from repository 17).

In step 407 image comparator 15 compares a first image difference metric with a Patient Identification and Recognition threshold. The first image difference metric represents a difference between a CTp (original planning data volume) image and a CTn=1 (a first treatment session data volume) image. In step 409 image comparator 15 compares a second image difference metric with a therapy Re-planning and optimization threshold. The second image difference metric represents a difference between a CTp (original planning data volume) image and a CTn=1 (a first treatment session data volume) image. The first and second metrics in one embodiment are the same and in another embodiment are different. In step 413 image comparator 15 compares a third image difference metric with a Patient Identification and Recognition threshold. The third image difference metric represents a difference between a CTn−1 (prior radiotherapy treatment session image volume) image and a CTn (a current session image volume) image. In step 417 image comparator 15 compares a fourth image difference metric with a therapy Re-planning and optimization threshold. The fourth image difference metric represents a difference between a CTp (most current planning image volume) image and a CTn (a current session image volume) image.

The processes depicted in FIGS. 2, 3 and 4 involve taking X-Ray volume images (CTp) to plan radiation oncology treatment that are compared with incremental images, CTn, taken throughout a course of radiation treatment. Image change detection measures, including differences or residuals between 3-D images (having a vector comprising a function of x, y, image number, and color data) are compared with a corresponding threshold vector. If the residual differences between a planning vector and the threshold vector are exceeded, an optimization warning in the form of a notification to re-assess planning based upon the current image, CTn, is provided as a message via a physician worklist to an attending Oncologist and Radiologist, for example. Planning images, CTp, are compared with incremental images, CTn, to determine the degree of sameness.

The degree of sameness of the images, is determined in one embodiment through a statistical distance measure comparing the normalized square of differences between the registered x- and y-coordinate points within the planning and incremental image, as well as the registered color differences. This provides a means of determining the likelihood or probability of correct patient association, Pa. The calculation in one embodiment involves a normalized distance measure, such a Mahalanobis distance, $c^2=S(Vp-Vn)^2+(Cp-Cn)^2$ where Vp−Vn represents luminance difference of corresponding x and y coordinate image elements within planning image p and incremental image n; Cp−Cn represents the color differences between the registered images p and n. A probability measure determined by the value of c with respect to a mean value (subject to distance of c from a mean relative to a Gaussian distribution) is used to establish the likelihood of similarity, otherwise known as the probability of correct association between any two images. The determined probability of correct association, Pa, of an incremental image with a planning image is used to establish the likelihood of correct association of one image with another image of the same anatomical portion of the same patient. This minimizes safety hazards associated with falsely associating two respective images of different patients. In the special case when n=1 only CTp exists. Subsequent comparisons between CTn and CTp are used to establish the likelihood that the most current image, is indeed associated with the correct patient. Such a measure of sameness is used to confirm whether a planning image is correct via repeated and consistent verification that subsequent images, CTn, are alike one another but are significantly different (defined statistically as exceeding a threshold on sameness) from the planning image, CTp.

Incremental images, CTn, are compared with incremental images, CTn−1, to determine the degree of sameness from one incremental image in comparison with respect to prior incremental images. The degree of sameness, as determined through the statistical distance measure comparing the normalized square of differences between the registered x and y coordinate point luminance and color differences within any prior incremental image with a current incremental image, provides a means of determining the likelihood or probability of correct patient association, Pa. The calculation is carried out using a normalized distance measure, such a Mahalanobis distance, $c^2=S(Vn-1-Vn)^2+(Cn-1-Cn)^2$, where Vn−1 and Vn represents luminance difference of corresponding x and y coordinate image elements within incremental image n−1 and incremental image n; Cn−1 and Cn represent the color differences between the registered images n−1 and n. The probability of correct association, Pa, of any incremental image with any other incremental image is used to determine the likelihood that images are correctly associated with the same patient and body portion. This reduces the safety hazard involved incorrectly associating two images of different patients or different body portions, for example.

System 10 (FIG. 1) advantageously provides an interventional procedure for patient identity verification and radiation therapy adjustment by comparing routinely (daily) acquired volumetric images, for example. Patient identification and therapy planning update verification determinations in one embodiment are made as a routine part of a patient imaging examination. System 10 generates a patient identification warning as an initial step prior to allowing therapy to proceed in order to notify a user that an incorrect patient may be about to receive treatment. System 10 also generates a therapy adjustment warning as an initial step in an imaging examination in order to notify a user that a patient may be about to receive an outdated or inappropriate treatment to the anatomy portion used in planning. System 10 advantageously takes advantage of the reality that patient alignment commonly occurs via computer-aided image comparison (e.g. using a known difference optimization algorithm), and there is typically some error (image difference) left when aligning a pair (of non-identical) image volumes. The system advantageously compares this difference, upon optimum image alignment, with a threshold for patient identification and radiotherapy re-planning. The system may use a variety of different algorithms and functions for determining image difference for use in patient identification and radiotherapy re-planning and aligns the images to minimize the difference.

System 10 uses different image difference algorithms or functions for determining patient identification and radiotherapy re-planning and in different embodiments may use the same or different patient identification and therapy adjustment thresholds. The difference between image volumes of two different patients (being compared with the patient identification threshold) is typically of greater magnitude than the difference of two image volumes of the same patient on different days (being compared with the re-planning threshold). In one embodiment, the image comparison process employed by image comparator 15 is the same for both patient identification and re-planning. However, since a different image volume is usually employed in patient identification than is employed in therapy re-planning, a computed patient identification image difference typically varies substantially from a computed re-planning image difference. Further, the more image pixels employed in an image comparison the larger is the variation.

Image comparator 15 captures raw pixel data of an X-Ray image and compares the raw data with raw pixel data of subsequent X-Ray images taken at later times during a normal radiotherapy treatment process. Several dozen X-Ray images may be taken and compared with previous images, for example. FIG. 6 illustrates a brief comparison between pixel data. Specifically, FIG. 6 illustrates a brief comparison between pixel data associated with a CTp image in column 605 with pixel data of a CTn image in column 610. The number of a pixel is given in column 603. The raw data (either the Haar-wavelet transformed image or the actual raw data itself) is presented in columns 605 and 610. Column 613 represents differences in the pixel elements between the CTp and CTn images. The pixel differences are determined following registration (alignment) of the images. Column 615 indicates the root-sum-square (RSS) of the differences of the pixels between the CTp and CTn images, computed as follows:

$$RSS_{j,j-1} = \frac{\sqrt{\sum_{i=1}^{n}[Pixel_i^j - Pixel_i^{j-1}]^2}}{\sqrt{\sum_{i=1}^{n} Pixel_i^j} \sqrt{\sum_{i=1}^{n} Pixel_i^{j-1}}}$$

RSS is also termed Normalized Energy of the differences between the pixel elements of an image j and its comparative image j−1. Large values of energy imply large differences in the images.

Figure 7:
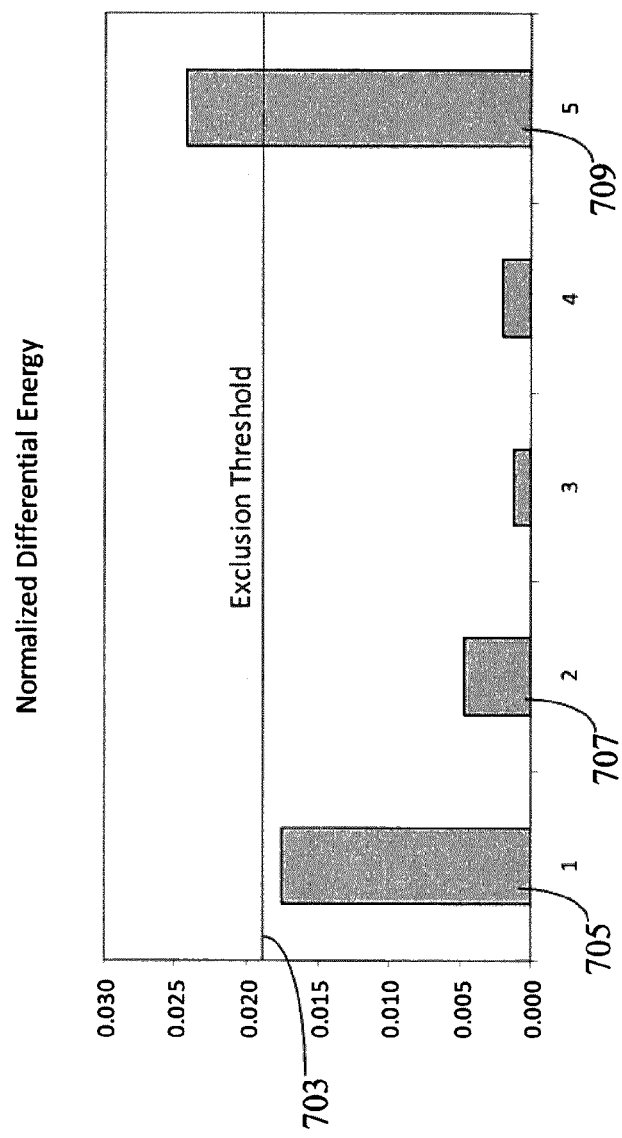
FIG. 7 illustrates image differences represented as energy values and image difference threshold setting, according to invention principles.

FIG. 7 illustrates image differences represented as energy values and the setting of an image difference threshold. The RSS energies associated with subsequent image comparisons are compared with a predetermined exclusion threshold 703. The normalized differential image energy for bar 705 represents the RSS between image 1 and image 0. Similarly, bar labeled 707 represents the RSS between image 2 and image 1 etc. Predetermined exclusion threshold 703 is derived based upon a priori knowledge of acceptable image differences. Image comparator 15 generates an alert indication message in response to image differential energy exceeding threshold 703 indicating either the two compared images are different (implying different patients) or there is a substantial difference between the two images implying change in a tumor, for example. Thus, the difference in the energy computed between images 5 and 4 represented by bar 709 shows a larger threshold differential than the image threshold, thereby indicating a significant change between images 5 and 4.

Figure 8:
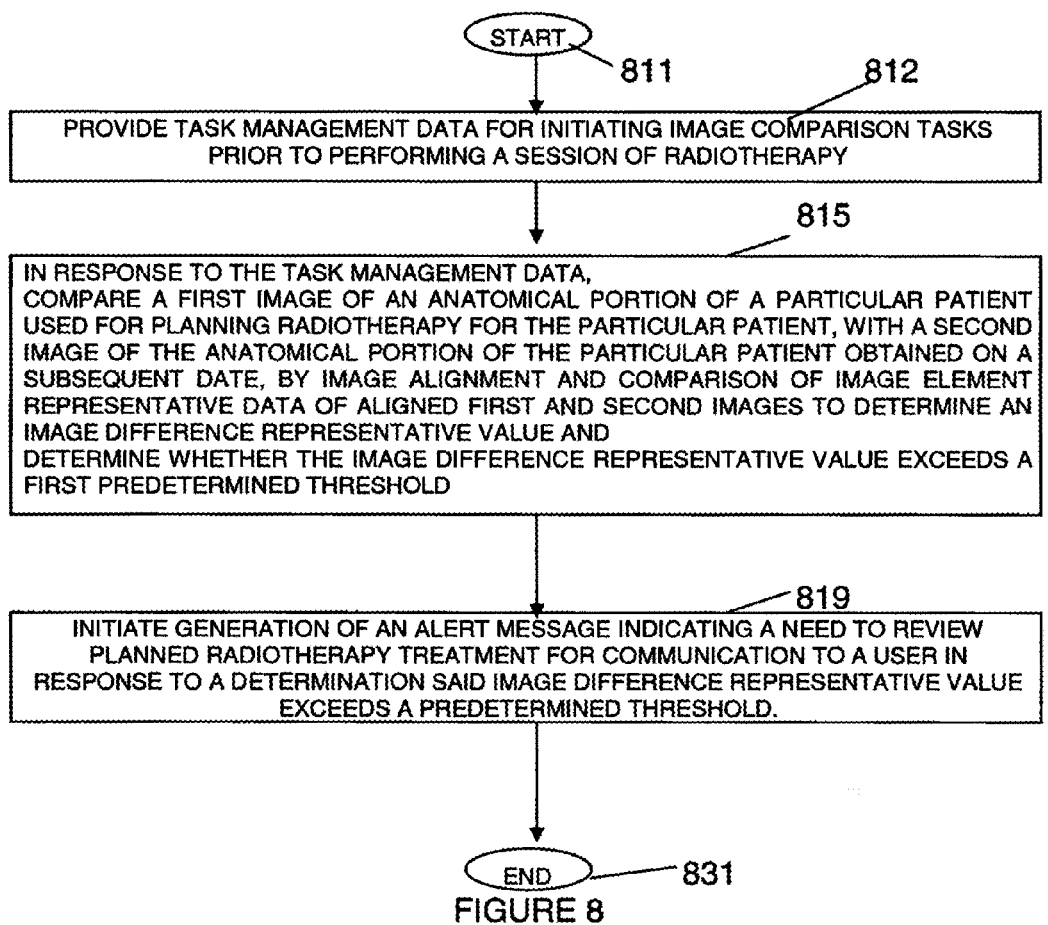
FIG. 8 shows a flowchart of a process performed by a medical radiation therapy and workflow system supporting review and update of radiotherapy treatment, according to invention principles.

FIG. 8 shows a flowchart of a process performed by medical radiation therapy and workflow system 10 supporting review and update of radiotherapy treatment. In step 812, following the start at step 811, task processor 34 (FIG. 1) provides task management data for initiating image comparison tasks prior to performing a session of radiotherapy. In step 815, image comparator 15, coupled to task processor 34, in response to the task management data, compares a first image of an anatomical portion of a particular patient used for planning radiotherapy for the particular patient, with a second image of the anatomical portion of the particular patient obtained on a subsequent date. Image comparator 15 compares the first and second images by image alignment and comparison of image element representative data of aligned first and second images to determine a first image difference representative value and determines whether the first image difference representative value exceeds a first predetermined threshold. Image comparator 15 compares a third image of the anatomical portion of the particular patient with a fourth image of the anatomical portion of the particular patient obtained on different dates, by image alignment and comparison of image element representative data of aligned third and fourth images to determine a second image difference representative value and determines whether the second image difference representative value exceeds a second predetermined threshold. Image comparator 15 also performs a second determination by determining whether the first image difference representative value exceeds a further predetermined threshold. In different embodiments, two or more of, the first, second and further predetermined thresholds may be the same or different and at least one of the first and second images, is the same as the third and fourth image.

In addition, an image element comprises at least one of, (a) an image pixel, (b) multiple pixels of an image and (c) a block of image pixels and the pixels may or may not be contiguous. The image element representative data may also comprise, image element luminance representative data values and image element color representative data values. Further, the image element luminance representative data values represent Computed Tomography grayscale image data, MR grayscale image data or another imaging modality device grayscale image data.

In step 819, output processor 19, coupled to image comparator 15, initiates generation of first and second alert messages. The first alert message indicates a need to review planned radiotherapy treatment for communication to a user in response to a determination the image difference representative value exceeds a first predetermined threshold. The second alert message indicates a need to check patient identity prior to radiotherapy treatment in response to a determination the second image difference representative value exceeds the second predetermined threshold. Output processor 19 inhibits administering radiotherapy in response to a determination the image difference representative value exceeds the first or second predetermined threshold. The process of FIG. 8 terminates at step 831.

The systems and processes of FIGS. 1-8 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. System 10 image comparison may be modified and applied to various phases of a medical image acquisition process. The processes and applications may, in alternative embodiments, be located on one or more (e.g., distributed) processing devices accessing a network linking the elements of FIG. 1. Further, any of the functions and steps provided in FIGS. 1-8 may be implemented in hardware, software or a combination of both and may reside on one or more processing devices located at any location of a network linking the elements of FIG. 1 or another linked network, including the Internet.

What is claimed is:
1. A medical radiation therapy and workflow system supporting review and update of radiotherapy treatment, comprising:
 a task processor for providing task management data for initiating image comparison tasks prior to performing a session of radiotherapy;
 an image comparator, coupled to said task processor, for, in response to said task management data, comparing a first image of an anatomical portion of a particular patient used for planning radiotherapy for said particular patient, with a second image of said anatomical portion of said particular patient obtained on a subsequent date, by image alignment and comparison of image element representative data of aligned first and second images to determine a first image difference representative value and determining whether said first image difference representative value exceeds a first predetermined threshold; and an output processor, coupled to said image comparator, for initiating generation of an alert message indicating a need to review planned radiotherapy treatment for communication to a user in response to a determination said first image difference representative value exceeds a predetermined threshold.

2. A system according to claim 1, wherein
said image difference representative value comprises an image difference representative remainder value.

3. A system according to claim 1, wherein
said output processor inhibits administering radiotherapy in response to said determination.

4. A system according to claim 1, wherein
an image element comprises at least one of, (a) an image pixel, (b) multiple pixels of an image and (c) a block of image pixels.

5. A system according to claim 4, wherein
said pixels are not contiguous.

6. A system according to claim 4, wherein
said image element representative data comprises at least one of, (a) image element luminance representative data values and (b) image element color representative data values.

7. A system according to claim 6, wherein
said image element luminance representative data values represent Computed Tomography grayscale image data.

8. A system according to claim 6, wherein
said image element luminance representative data values represent MR grayscale image data.

9. A system according to claim 6, wherein
said image element luminance representative data values represent imaging modality device grayscale image data.

10. A system according to claim 1, wherein
said image comparator perform a second determination by determining whether said first image difference representative value exceeds a further predetermined threshold and said output processor initiates generation of an alert message indicating a need to check patient identity prior to radiotherapy treatment.

11. A system according to claim 10, wherein
said first and further predetermined thresholds are the same.

12. A system according to claim 1, wherein
said image comparator compares a third image of said anatomical portion of said particular patient with a fourth image of said anatomical portion of said particular patient obtained on different dates, by image alignment and comparison of image element representative data of aligned third and fourth images to determine a second image difference representative value and determines whether said second image difference representative value exceeds a second predetermined threshold and said output processor initiates generation of an alert message indicating a need to check patient identity prior to radiotherapy treatment in response to a determination said second image difference representative value exceeds said second predetermined threshold.

13. A system according to claim 12, wherein
at least one of said first and second images is the same as the third and fourth image.

14. A system according to claim 12, wherein
said first and second predetermined thresholds are the same.

15. A medical radiation therapy and workflow system supporting review and update of radiotherapy treatment, comprising:

a task processor for providing task management data for initiating image comparison tasks prior to performing a session of radiotherapy;

an image comparator, coupled to said task processor, for, in response to said task management data, comparing a first image of said anatomical portion of said particular patient with a second image of said anatomical portion of said particular patient obtained on different dates, by image alignment and comparison of image element representative data of aligned first and second images to determine an image difference representative value and determining whether said image difference representative value exceeds a predetermined threshold and an output processor, coupled to said image comparator, for initiating generation of an alert message indicating a need to check patient identity prior to radiotherapy treatment in response to a determination said image difference representative value exceeds said predetermined threshold.

16. A system according to claim 15, wherein
said image comparator compares a third image of said anatomical portion of a particular patient used for planning radiotherapy for said particular patient, with a fourth image of said anatomical portion of said particular patient obtained on a subsequent date, by image alignment and comparison of image element representative data of aligned third and fourth images to determine a second image difference representative value and determines whether said second image difference representative value exceeds a second predetermined threshold; and said output processor initiates generation of an alert message indicating a need to review planned radiotherapy treatment for communication to a user in response to a determination said second image difference representative value exceeds said second predetermined threshold.

17. A system according to claim 16, wherein
said first and second predetermined thresholds are the same.

* * * * *